United States Patent [19]
Guss et al.

[11] Patent Number: 5,756,670
[45] Date of Patent: May 26, 1998

[54] METHOD AND MEANS FOR PRODUCING AN IMMUNOGLOBULIN-BINDING PROTEIN

[75] Inventors: Bengt Mikael Guss, Uppsala; Jan Ingmar Flock, Bromma; Martin Kjell Lindberg; Mathias Carl Erik Uhlen, both of Uppsala, all of Sweden

[73] Assignee: Pharmacia Biotech Aktiebolag, Uppsala, Sweden

[21] Appl. No.: 467,172

[22] Filed: Jun. 6, 1995

Related U.S. Application Data

[62] Division of Ser. No. 355,133, Apr. 16, 1989, which is a continuation of Ser. No. 130,995, Nov. 6, 1987, abandoned.

[30] Foreign Application Priority Data

Mar. 21, 1986 [SE] Sweden .................. 8601325

[51] Int. Cl.$^6$ .................... C07K 19/00
[52] U.S. Cl. .................... 530/350; 435/69.7; 435/971; 536/23.4
[58] Field of Search .................... 330/350; 435/69.7, 435/971; 536/23.4

[56] References Cited

U.S. PATENT DOCUMENTS

| | | | |
|---|---|---|---|
| 4,038,140 | 7/1977 | Jaworek et al. | 195/63 |
| 4,617,266 | 10/1986 | Fahnestock | 435/68 |
| 4,704,366 | 11/1987 | Juarez-Salinas et al. | 436/501 |
| 4,900,660 | 2/1990 | Boyle et al. | 435/7 |
| 4,945,157 | 7/1990 | Boyle et al. | 530/409 |
| 4,948,874 | 8/1990 | Kronvall et al. | 530/350 |
| 4,954,618 | 9/1990 | Fahnestock | 530/387 |
| 4,956,296 | 9/1990 | Fahnestock | 435/252.33 |
| 4,977,247 | 12/1990 | Fahnestock et al. | 530/387 |
| 5,082,773 | 1/1992 | Fahnestock | 435/69.1 |
| 5,100,788 | 3/1992 | Löfdahl et al. | 435/69.7 |
| 5,108,894 | 4/1992 | Björck et al. | 435/6 |

FOREIGN PATENT DOCUMENTS

| | | |
|---|---|---|
| 0 107 509 | 5/1984 | European Pat. Off. |
| 0 124 374 | 11/1984 | European Pat. Off. |
| 0 131 142 | 1/1985 | European Pat. Off. |
| 0 200 909 | 12/1986 | European Pat. Off. |
| 0 284 368 | 9/1988 | European Pat. Off. |
| WO 84/03103 | 8/1984 | WIPO |
| WO 87/05025 | 8/1987 | WIPO |
| WO 87/05631 | 9/1987 | WIPO |

OTHER PUBLICATIONS

Åkerström et al., "Protein G: A Powerful Tool for Binding and Detection of Monoclonal and Polyclonal Antibodies", *J. Immunol.* 135(4):2589–2592 (Oct., 1985).

Åkerström et al., "A Physicochemical Study of Protein G, a Molecule with Unique Immunoglobulin G–Binding Properties", *J. Biol. Chem.* 261(22):10240–12047 (Aug. 5, 1986).

Björck et al., "Purification and Some Properties of Streptococcal Protein G, a Novel IgG–Binding Reagent", *J. Immunol.* 133(2):969–974 (1984).

Björck et al., "Streptococcal Protein G, Expressed by Streptococci or by *Escherichia coli*, has Separate Binding Sites for Human Albumin and IgG", *Molec. Immunol.* 24(10):1113–1122 (1987).

Boyle, M.D.P., "Applications of Bacterial Fc Receptors in Immunotechnology", *BioTechniques* 2(5):334–340 (1984).

Christensen et al., "Purification of Immunoglobulin G Fc–Reactive Factor From *Streptococcus agazardah*", *Acta Path. Microbiol. Scand. Sect. C* 84:196–202 (1976).

(List continued on next page.)

*Primary Examiner*—Mary E. Mosher
*Attorney, Agent, or Firm*—Sterne, Kessler, Goldstein & Fox, PLLC

[57] ABSTRACT

Method for producing a protein having the same IgG specificity as protein G from group G Streptococci, strain G148. The invention also relates to a recombinant DNA molecule coding for said protein, and to microorganisms containing this recombinant DNA molecule. The invention also relates to a recombinant DNA molecule coding for a protein having the IgG binding specificity of both protein G and protein A.

2 Claims, 9 Drawing Sheets

OTHER PUBLICATIONS

Claverys et al., "Cloning of *Streptococcus pneumoniae* DNA: Its Use in Pneumococcal Transformation and in Studies of Mismatch Repair", *Gene* 13:65–73 (1981).

Colbert, D. et al., "Molecular Organization of the Protein A Gene and Its Expression in Recombinant Host Organisms", *J. Biol. Resp. Mod.* 3:255–250 (1984).

Eliasson et al., "Chimeric IgG–Binding Receptors Engineered from Staphylococcal Protein A and Streptococcal Protein G", *J. Biol. Chem.* 263(9):4323–4327 (1988).

Erntell et al., "Streptococcal Protein G has Affinity for Both Fab– and Fc–Fragments of Human IgG", *Molec. Immunol.* 25(2):121–126 (1988).

Fahnestock et al., "Gene for an Immunoglobulin–Binding Protein from a Group G Streptococcus", *J. Bacteriol.* 167(3):870–880 (Sep., 1986).

Fahnestock, S.R., "Cloned Streptococcal Protein G Genes", *Tibtech* 5:79–83 (1987).

Gilpin et al., "Cloning and Expression of Two *Streptococcus mutans* Glucosyltransferases in *Escherichia coli* K–12", *Infect. and Immun.* 49(2):414–416 (Aug., 1985).

Guss et al., "Structure of the IgG–Binding Regions of Streptococcal Protein G", *Embo J.* 5(7):1567–1575 (Jul., 1986).

Holt et al., "*Streptococcus mutans* Genes that Code for Extracellular Proteins in *Escherichia coli* K–12", *Infec. and Immun.* 38(1):147–156 (1982).

Kronvall, G., "A Surface Component in Group A, C, and G Streptococci with Non–Immune Reactivity for Immunoglobulin G", *J. Immunol.* 111:1401–1406 (1973).

Löfdahl et al., "Gene for Staphylococcal Protein A", *Proc. Natl. Acad. Sci. USA* 80:697–701 (1983).

Malke et al., "Streptokinase: Cloning, Expression, and Excretion by *Escherichia coli*", *Proc. Natl. Acad. Sci. USA* 81:3557–3561 (1984).

Myhre et al., "Heterogeneity of Nonimmune Immunoglobulin Fc Reactivity Among Gram–Positive Cocci: Description of Three Major Types of Receptors for Human Immunoglobulin G", *Infec. and Immun.* 17(3):475–482 (1977).

Myhre et al., "Immunolgbulin–Binding Structure on Bovine Group G Streptococci Different from Type III Fc Receptors on Human Group G Streptococci", *Infec. and Immun.* 23(1):1–7 (1979).

Nilsson, B. et al., "Immobilization and Purification of Enzymes with Staphylococcal Protein A Gene Fusion Vectors", *EMBO J.* 4(4):1075–1080 (Apr., 1985).

Olsson et al., "Structure and Evolution of the Repetitive Gene Encoding Streptococcal Protein G", *Eur. J. Biochem.* 168:319–324 (1987).

Reis et al., "Streptococcal Fc Receptors. I. Isolation and Partial Characterization of the Receptor from a Group C Streptococcus", *J. Immunol.* 132(6):3091–3097 (1984).

Reis et al., "Streptococcal Fc Receptors. II. Comparison of the Reactivity of a Receptor from a Group C Streptococcus With Staphylococcal Protein A", *J. Immunol.* 132(6):3098–3102 (1984).

Reis et al., "Extraction and Characterization of IgG Fc Receptors from Group C and Group G Streptococci", *Molec. Immunol.* 23(4):425–431 (Apr., 1986).

Russell et al., "Expression of a Gene for Glucan–Binding Protein from *Streptococcus mutans* in *Escherichia coli*", *J. Gen. Microbiol.* 131(2):295–299 (Feb., 1985).

Russell et al., "Cloning of Sucrase Genes from *Streptococcus mutans* in Bacteriophage Lambda", *FEMS Microbiol. Lett.* 30(1/2):37–41 (Oct./Nov., 1985).

Schalén et al., "Binding of Aggregated IgG Fab–Fragments and Light Chains to Some Group A, C and G Streptococci", *Acta Path. Microbiol. Immunol. Scand. B* B 91:27–33 (1983).

Shea et al., "Examination of *Streptococcus mutans* for Immunoglobulin G Fc Reactivity", *Infec. and Immun.* 34(3):851–855 (1981).

Sjöbring et al., "Isolation and Characterization of a 14–kDa Albumin–Binding Fragments of Streptococcal Protein G", *J. Immunol.* 140(5):1595–1599 (1988).

Uhlén, M. et al., "The Gene for Staphylococcal Protein A", *Immunol. Today* 5(8):244–248 (1984).

von Mering et al., "Comparison of Type III Fc Receptors Associated with Group C and Group G Streptococci", *Molec. Immunol.* 23(8):811–821 (Aug., 1986).

```
EcoRI            ┌──► A1
GAA TTC AAC AAA TAT GGA GTA AGT GAC TAT TAC AAG AAT CTA ATC    45
Glu Phe Asn Lys Tyr Gly Val Ser Asp Tyr Tyr Lys Asn Leu Ile

┌──► B1
AAC AAT GCC AAA ACT GTT GAA GGC GTA AAA GAC CTT CAA GCA CAA    90
Asn Asn Ala Lys Thr Val Glu Gly Val Lys Asp Leu Gln Ala Gln

GTT GTT GAA TCA GCG AAG AAA GCG CGT ATT TCA GAA GCA ACA GAT   135
Val Val Glu Ser Ala Lys Lys Ala Arg Ile Ser Glu Ala Thr Asp

GGC TTA TCT GAT TTC TTG AAA TCA CAA ACA CCT GCT GAA GAT ACT   180
Gly Leu Ser Asp Phe Leu Lys Ser Gln Thr Pro Ala Glu Asp Thr

GTT AAA TCA ATT GAA TTA GCT GAA GCT AAA GTC TTA GCT AAC AGA   225
Val Lys Ser Ile Glu Leu Ala Glu Ala Lys Val Leu Ala Asn Arg

┌──►A2
GAA CTT GAC AAA TAT GGA GTA AGT GAC TAT CAC AAG AAC CTA ATC   270
Glu Leu Asp Lys Tyr Gly Val Ser Asp Tyr His Lys Asn Leu Ile

┌──► B2
AAC AAT GCC AAA ACT GTT GAA GGT GTA AAA GAC CTT CAA GCA CAA   315
Asn Asn Ala Lys Thr Val Glu Gly Val Lys Asp Leu Gln Ala Gln

GTT GTT GAA TCA GCG AAG AAA GCG CGT ATT TCA GAA GCA ACA GAT   360
Val Val Glu Ser Ala Lys Lys Ala Arg Ile Ser Glu Ala Thr Asp

GTT AAA TCA ATT GAA TTA GCT GAA GCT AAA GTC TTA GCT AAC AGA   450
Val Lys Ser Ile Glu Leu Ala Glu Ala Lys Val Leu Ala Asn Arg

┌──►A3
GAA CTT GAC AAA TAT GGA GTA AGT GAC TAT TAC AAG AAC CTA ATC   495
Glu Leu Asp Lys Tyr Gly Val Ser Asp Tyr Tyr Lys Asn Leu Ile

┌──►S
AAC AAT GCC AAA ACT GTT GAA GGT GTA AAA GCA CTG ATA GAT GAA   540
Asn Asn Ala Lys Thr Val Glu Gly Val Lys Ala Leu Ile Asp Glu
```

FIG.2a

```
                                    ┌─── C1
ATT TTA GCT GCA TTA CCT AAG ACT GAC ACT TAC AAA TTA ATC CTT   585
Ile Leu Ala Ala Leu Pro Lys Thr Asp Thr Tyr Lys Leu Ile Leu

AAT GGT AAA ACA TTG AAA GGC GAA ACA ACT ACT GAA GCT GTT GAT   630
Asn Gly Lys Thr Leu Lys Gly Glu Thr Thr Thr Glu Ala Val Asp

Pst I
GCT GCT ACT GCA GAA AAA GTC TTC AAA CAA TAC GCT AAC GAC AAC   675
Ala Ala Thr Ala Glu Lys Val Phe Lys Gln Tyr Ala Asn Asp Asn

GGT GTT GAC GGT GAA TGG ACT TAC GAC GAT GCG ACT AAG ACC TTT   720
Gly Val Asp Gly Glu Trp Thr Tyr Asp Asp Ala Thr Lys Thr Phe

┌─── D1          Cla I
ACA GTT ACT GAA AAA CCA GAA GTG ATC GAT GCG TCT GAA TTA ACA   765
Thr Val Thr Glu Lys Pro Glu Val Ile Asp Ala Ser Glu Leu Thr

┌─── C2
CCA GCC GTG ACA ACT TAC AAA CTT GTT ATT AAT GGT AAA ACA TTG   810
Pro Ala Val Thr Thr Tyr Lys Leu Val Ile Asn Gly Lys Thr Leu

Pst I
AAA GGC GAA ACA ACT ACT GAA GCT GTT GAT GCT GCT ACT GCA GAA   855
Lys Gly Glu Thr Thr Thr Glu Ala Val Asp Ala Ala Thr Ala Glu

AAA GTC TTC AAA CAA TAC GCT AAC GAC AAC GGT GTT GAC GGT GAA   900
Lys Val Phe Lys Gln Tyr Ala Asn Asp Asn Gly Val Asp Gly Glu

┌─── D2
TGG ACT TAC GAC GAT GCG ACT AAG ACC TTT ACA GTT ACT GAA AAA   945
Trp Thr Tyr Asp Asp Ala Thr Lys Thr Phe Thr Val Thr Glu Lys

Cla I                                         ┌─── C3
CCA GAA GTG ATC GAT GCG TCT GAA TTA ACA CCA GCC GTG ACA ACT   990
Pro Glu Val Ile Asp Ala Ser Glu Leu Thr Pro Ala Val Thr Thr

TAC AAA CTT GTT ATT AAT GGT AAA ACA TTG AAA GGC GAA ACA ACT   1035
Tyr Lys Leu Val Ile Asn Gly Lys Thr Leu Lys Gly Glu Thr Thr
```

FIG.2b

```
                       PstI
ACT AAA GCA GTA GAC GCA GAA ACT GCA GAA AAA GCC TTC AAA CAA   1080
Thr Lys Ala Val Asp Ala Glu Thr Ala Glu Lys Ala Phe Lys Gln

TAC GCT AAC GAC AAC GGT GTT GAT GGT GTT TGG ACT TAT GAT GAT   1125
Tyr Ala Asn Asp Asn Gly Val Asp Gly Val Trp Thr Tyr Asp Asp

┌─ W
GCG ACT AAG ACC TTT ACG GTA ACT GAA ATG GTT ACA GAG GTT CCT   1170
Ala Thr Lys Thr Phe Thr Val Thr Glu Met Val Thr Glu Val Pro

Hpa I
CTT GTT CCG TTA ACT CCT GCA ACT CCA ATT GCT AAA GAT GAC GCT   1260
Leu Val Pro Leu Thr Pro Ala Thr Pro Ile Ala Lys Asp Asp Ala

AAG AAA GAC GAT ACT AAG AAA GAA GAT GCT AAA AAA CCA GAA GCT   1305
Lys Lys Asp Asp Thr Lys Lys Glu Asp Ala Lys Lys Pro Glu Ala

AAG AAA GAA GAC GCT AAG AAA GCT GAA ACT CTT CCT ACA ACT GGT   1350
Lys Lys Glu Asp Ala Lys Lys Ala Glu Thr Leu Pro Thr Thr Gly

┌─ M          PvuII
GAA GGA AGC AAC CCA TTC TTC ACA GCA GCT GCG CTT GCA GTA ATG   1395
Glu Gly Ser Asn Pro Phe Phe Thr Ala Ala Ala Leu Ala Val Met

GCT GGT GCG GGT GCT TTG GCG GTC GCT TCA AAA CGT AAA GAA GAC   1440
Ala Gly Ala Gly Ala Leu Ala Val Ala Ser Lys Arg Lys Glu Asp

HindIII
TAA TTGTCATTATTTTTGACAAAAAGCTT                                 1469
***
```

FIG.2c

```
        ACT TAC AAA TTA ATC CTT AAT GGT AAA ACA TTG AAA GGC GAA ACA ACT
    C1  Thr Tyr Lys Leu Ile Leu Asn Gly Lys Thr Leu Lys Gly Glu Thr Thr
    C2   -   -   -   *  Val Ile  -   -   -   -   -   -   -   -   -   -
    C3   -   -   -   *  Val Ile  -   -   -   -   -   -   -   -   -   -

ACT GAA GCT GTT GAT GCT GCT ACT GCA GAA AAA GTC TTC AAA CAA TAC
    C1  Thr Glu Ala Val Asp Ala Ala Thr Ala Glu Lys Val Phe Lys Gln Tyr
    C2   -   -   -   -   -   -   -   -   -   -   -   -   -   -   -   -
    C3   -  Lys  *   *   *   *  Glu  -   -   -   -  Ala  -   -   -   -

GCT AAC GAC AAC GGT GTT GAC GGT GAA TGG ACT TAC GAC GAT GCG ACT
    C1  Ala Asn Asp Asn Gly Val Asp Gly Glu Trp Thr Tyr Asp Asp Ala Thr
    C2   -   -   -   -   -   -   -   -   -   -   -   -   -   -   -   -
    C3   -   -   -   -   -   -   -   -  Val  -   -   *   *   -   -   -

AAG ACC TTT ACA GTT ACT GAA           AAA CCA GAA GTG ATC GAT GCG
    C1  Lys Thr Phe Thr Val Thr Glu       D1  Lys Pro Glu Val Ile Asp Ala
    C2   -   -   -   -   -   -   -       D2   -   -   -   -   -   -   -
    C3   -   -   -   -   *   *   -

TCT GAA TTA ACA CCA GCC GTG ACA
    D1  Ser Glu Leu Thr Pro Ala Val Thr
    D2   -   -   -   -   -   -   -   -
```

METHOD AND MEANS FOR PRODUCING AN IMMUNOGLOBULIN-BINDING PROTEIN

This application is a division, of application Ser. No. 07/355,133, filed May 16, 1989, which is a continuation of application No. 07/130,995, filed Nov. 6, 1987, abandoned.

BACKGROUND OF THE INVENTION

The invention relates to the field of gene technology and is concerned with recombinant DNA molecules, which contain a nucleotide sequence coding for a protein or polypeptide of the same IgG specificity as protein G from group G Streptococci strain G148. Moreover the invention comprises microorganisms containing the aforesaid molecules, and the use thereof in the production of the aforesaid protein or polypeptide.

The existence of bacterially produced proteins or polypeptides binding selectively to the Fc portion of immunoglobulins has been known for decades. Among such proteins the one that has been investigated most thoroughly is protein A from *Staphylococcus aureus;* and this is actually the only protein of that group which has acquired commercial importance (Protein A and Protein A Sepharose® from Pharmacia AB, Uppsala, Sweden). Sjöquist (FEBS Letters 28 (1) (1972) p. 73–76 and U.S. Pat. Nos. 3,850,798 and 3,995,018) made the discovery that one component of the protein A-IgG system when immobilized on an insoluble polymer could be employed for binding the other component, and it became thus possible to purify the protein on a large scale and, also, to develop a very simple and selective method for the isolation of antibodies. The specificity of the protein for various different immunoglobulins has been studied in great detail; see for instance Forsgren, A. et al., Staphylococci and Staphylococcal Infections 2 (1983), p. 429–479, Academic Press Inc. (London). A remarkable feature of that protein is its low affinity for the IgG subclass IgG$_3$ of the human system. In view of the fact that this subclass amounts to about 8% of the total IgG content in serum supplementary purification steps are required for isolating all classes of IgG.

SUMMARY OF THE INVENTION

However, already in 1973 Kronvall (J. Immunol. 111(5) (1973) p. 1401–6) showed that also group C and G Streptococci carry components on their surface which have affinity for IgG. The experiments furthermore showed that their reactivity in this respect was a non-immunoreactivity, that is, the immunoglobulin was not bound via its antigen combining sites in the Fab portions, and the results indicated that IgG$_3$ too was bound in this system. This Fc-binding component has later on been found to be of a protein nature and has been given the name of "protein G". Therefore, as a supplement to the *Staphylococcus aureus* protein A or as a total or partial replacement thereof, protein G would be a natural choice among bacterially produced proteins capable of binding to the Fc portion of IgG class immunoglobulins, for example for the purpose of purifying IgG (U.S. Pat. No. 3,995,018). But the protein has not been studied to any major extent, due to problems involved with its liberation from the bacterium.

In Journal of Immunol. 133(2) p. 969 Bjorck and Kronvall in 1984 published a method by which small amounts of the protein were set free from the bacterium by means of enzymatic degradation with papain. This method will give a material enabling limited functional and structural studies to be carried out, but the yields are far too low for commercial use, e.g. for the purification of monoclonal antibodies. Quite generally also it may be difficult to obtain a homogeneous and reproducible product with such a method. Moreover Streptococci are pathogenic and necessitate the use of complex culturing media which involve complications in large-scale cultures. There is thus a need for a new method of producing Fc-binding proteins or fragments thereof from Streptococci of types C and G.

The present invention relates to a recombinant DNA molecule comprising a nucleotide sequence which codes for a protein or polypeptide having the same IgG specificity as protein G from group G Streptococci strain G148. The natural source of this nucleotide sequence is of course the said bacterial strain, but quite conceivably also recourse may be had to synthetically produced molecules, in particular for the active polypeptides. The term "active polypeptides" in this context refers to polypeptides that have the aforesaid IgG specificity.

For producing a recombinant DNA molecule according to the invention a suitable cloning vehicle or vector, for example a plasmid or phage DNA, may be cleaved with the aid of a restriction enzyme whereupon the DNA sequence coding for the desired protein or polypeptide is inserted into the cleavage site to thus form the recombinant DNA molecule. This general procedure is known per se, and various techniques for cleaving and ligating DNA sequences have been described in the literature (see for instance U.S. Pat. No. 4,237,224); but to the best of our knowledge these techniques have not been used in the present protein system. If the bacterial strain Streptococcus G148 is employed as the source of the desired nucleotide sequence it is possible to isolate said sequence and to introduce it into a suitable vector in a manner such as described in the experimental part below.

Hosts that may be employed—that is, microorganisms which are caused to produce the protein or active fragments thereof—may comprise bacterial hosts such as strains of e.g. Escherichia, Bacillus, Streptococcus, Staphylococcus and furthermore yeasts and other eukaryotic cells in culture. Among bacterial hosts those of the gram-positive type are preferred because of the fact that their cell wall contains only one membrane system. If the protein or the active fragment is produced in combination with a signal peptide suiting the system then the product is directly secreted into the medium. Numerous signal peptides have been published during recent years, see for example WO 84/00774; to persons skilled in the art it is a matter of well-known routine to choose and employ signal peptides apt to give a good secretion in various bacterial systems. For obtaining maximum expression, regulatory elements such as promoters and ribosome-binding sequences may be varied in a manner known per se.

The invention thus comprises recombinant DNA molecules containing a nucleotide sequence which codes for a protein or polypeptide having the same IgG specificity as protein G from Streptococcus G148. As will be seen from the experimental portion of this specification the protein G gene has the following nucleotide sequences C1, C2 and C3 coding for IaG-binding polypeptides:

C1
```
ACT TAC AAA TTA ATC CTT AAT GGT AAA ACA TTG AAA GGC GAA ACA
ACT ACT GAA GCT GTT GAT GCT GCT ACT GCA GAA AAA GTC TTC AAA
CAA TAC GCT AAC GAC AAC GGT GTT GAC GGT GAA TGG ACT TAC GAC
GAT GCG ACT AAG ACC TTT ACA GTT ACT GAA
```

C2
```
ACT TAC AAA CTT GTT ATT AAT GGT AAA ACA TTG AAA GGC GAA ACA
ACT ACT GAA GCT GTT GAT GCT GCT ACT GCA GAA AAA GTC TTC AAA
CAA TAC GCT AAC GAC AAC GGT GTT GAC GGT GAA TGG ACT TAC GAC
GAT GCG ACT AAG ACC TTT ACA GTT ACT GAA
``` and C3
```
ACT TAC AAA CTT GTT ATT AAT GGT AAA ACA TTG AAA GGC GAA ACA
ACT ACT AAA GCA GTA GAC GCA GAA ACT GCA GAA AAA GCC TTC AAA
CAA TAC GCT AAC GAC AAC GGT GTT GAT GGT GTT TGG ACT TAT GAT
GAT GCG ACT AAG ACC TTT ACG GTA ACT GAA
```

The invention thus relates to recombinant DNA molecules which contain one or more of the said nucleotide sequences or analogous sequences. The term "analogous sequences" means sequences coding for polypeptides of the aforesaid IgG specificity.

Furthermore the invention comprises vectors such as e.g. plasmids and phages containing such a nucleotide sequence, and microorganisms, especially bacteria as e.g. strains of Escherichia, Bacillus and Staphylococcus, into which such a vector has been introduced. Alternatively, such a nucleotide sequence may be integrated into the natural gene material of the microorganism.

The application furthermore relates to a method for the production of a protein or polypeptide having the same IgG specificity as protein G from Streptococcus G148. According to this method, a microorganism as set forth above is cultured in a suitable medium whereupon the resultant product is isolated by affinity chromatographic purification with the aid of IgG bound to an insoluble carrier, or by means of some other separating method, for example ion exchange chromatography.

Vectors, especially plasmids, which contain the protein G-encoding nucleotide sequence may advantageously be provided with a readily cleavable restriction site by means of which a nucleotide sequence that codes for another product can be fused to the protein G-encoding nucleotide sequence, to thus express a so-called fusion protein. The fusion protein may be isolated by a procedure utilizing its capacity of binding to IgG, whereupon the other component of the system may if desired be liberated from the fusion protein. This technique has been described at length in WO 84/03103 in respect of the protein A system and is applicable also in the present context in an analogous manner. Since protein G and protein A have binding properties partially complementary to each other a fusion protein containing both of these components is a potentially attractive product.

In one aspect of the invention a nucleotide sequence as defined above is fused to a gene sequence coding for protein A or an active fragment thereof in a fusion vector and accordingly in one molecule coding for a fusion protein with combined protein A and protein G binding characteristics. Vectors and microorganisms as defined above but containing this specific nucleotide sequence is another aspect of the invention. A further aspect is the fusion protein or polypeptide having the combined protein A and protein G binding characteristics, encoded by said nucleotide sequence or produced in an equivalent way.

STARTING MATERIALS AND GENERAL PROCEDURES

Streptococcus G148 which is a human group G strain was obtained from Statens Veterinärmedicinska Anstalt (SVA), Uppsala, Sweden.

E. coli strains HB101 (Boyer, HW and Roulland-Dussoix, D, J. Mol. Biol. 41(1969) p. 459–472 and JM 105 (Messing, J. and Carlsson, J., J. Biotechnol. 1(1984) p. 253–264 were employed as bacterial hosts for the plasmids to be constructed; and the strains NM538 and NM539 were used in cloning with the lambda vector EMBL3a (Frischauf, A-M et al., J. Mol. Biol. 170(1983) p. 827–842. The plasmid vectors employed were pUC13, pUC18, and pUC19 (Norrander, J. et al., Gene 26(1983), p. 101–106), and pBR322 (Bolivar, F et al. Gene 2 (1977) p. 95–113.

Culture media

The medium set forth below is employed for culturing E. coli bacteria. Amounts as stated are per 1 liter of medium.

| | |
|---|---|
| Trypton Soy Broth (Oxoid Ltd Basingstoke, Hants., England) | 30 g |
| Yeast Extract (Oxoid) | 10 g |
| D-glucose | 40 g |
| NH$_4$Cl | 2.5 g |
| Na$_2$HPO$_4$.2H$_2$O | 7.5 g |
| KH$_2$PO$_4$ | 3.0 g |
| Na$_2$SO$_4$.10H$_2$O | 2.5 g |
| MgSO$_4$.7H$_2$O | 0.2 g |

-continued

| | |
|---|---|
| $CaCl_2 \cdot 2H_2O$ | 0.5 mg |
| $FeCl_3 \cdot 6H_2O$ | 16.7 mg |
| $ZnSO_4 \cdot 7H_2O$ | 0.18 mg |
| $CuSO_4 \cdot 5H_2O$ | 0.16 mg |
| $MnSO_4 \cdot 4H_2O$ | 0.15 mg |
| $CoCl_2$ | 0.10 mg |
| NaEDTA | 20.1 mg |

The medium set forth below is employed for culturing Streptococcus G148. Here again, the amounts refer to the contents per 1 liter of culture medium.

| | |
|---|---|
| Yeast Extract (Oxoid) | 50 g |
| Trypton Soy Broth (Oxoid) | 30 g |
| L-alanine | 0.69 g |
| L-asparagine | 0.30 g |
| L-arginine | 0.50 g |
| L-glutamine | 0.43 g |
| glycine | 0.28 g |
| L-histidine | 0.15 g |
| L-isoleucine | 0.22 g |
| L-leucine | 0.33 g |
| L-lysine | 0.27 g |
| L-methionine | 0.09 g |
| L-phenylalanine | 0.35 g |
| L-proline | 0.50 g |
| L-serine | 0.26 g |
| L-threonine | 0.20 g |
| L-tryptophan | 0.07 g |
| L-tyrosine | 0.03 g |
| L-valine | 0.26 g |

DNA preparations

Streptococcus G148 cells were cultured in Todd-Hewitt medium (Oxoid Ltd Basingstoke, Hants., England). The cells were washed and then resuspended in a cell-free medium from Streptomyces griseus 9179 (1/20 of the original volume), whereupon lysozyme was added to a concentration of 1 mg/ml. The Streptomyces strain which had been obtained from Dr. W. Kohler, Institute fur Mikrobiologie und experimentelle Therapie, Jena, DDR) had been cultured in the manner as described by Prauser and Köhler in Zeitschrift für allg. Mikrobiologie vol. 5(4)(1965) p. 308–314 for inducing lytic activity. When the Streptococcus cells had been incubated in the medium for 2 hours at 37° C, the DNA was extracted as described by Marmur, J, J. Mol. Biol. 3(1961) p. 208–218.

Plasmid DNA from *E. coli* was prepared by alkaline extraction (Birnboim, H. C. et al. Nucleic Acids Res. 7(1979) p. 1513–1523).

Lambda DNA was prepared as described by Maniatis et al. (Molecular Cloning: A Laboratory Manual, Cold Spring Harbor Laboratory, New York 1982).

Plasmid transformations were performed as described by Morrison et al. (Methods Enzymol. 68(1979) p. 326–331).

Restriction endonucleases, T4 DNA ligase, DNA polymerase I and Klenow fragments were obtained from New England Biolabs (Boston, USA) or from Boehringer Mannheim (Mannheim, Federal Replublic of Germany) and were employed in conformity with the manufacturers' directions.

Example 1. Isolation of a lambda clone which codes for polypeptides possessing IgG-binding activity A gene library for Streptococcus G148 was produced in a manners analogous to that described by Frischauf et al. (1983, see above).

Streptococcal DNA was partially digested with Sau3A and ligated into BamHfI-cleaved lambda vector EMBL3a. The ligated DNA was packaged in vitro into phage particles which were then allowed to infect *E. coli* NM539 cells. The resultant phage library was analyzed for IgG-binding activity, the phages being titrated for this purpose on agar plates which were incubated overnight at 37° C. The next day plates having a plaque frequency of $10^3$–$10^4$ were selected. A nitrocellulose filter (Schleicher & Schüll, Membranefilter BA85 (0.45 micrometer) Dassel, Federal Republic of Germany) was placed onto each of these selected plates. Blotting was allowed to proceed at room temperature for about 10 minutes, whereupon the filters were immersed for 1 hour in phosphate-buffered sodium chloride solution (PBS) containing Tween 20 to 0.1% concentration. The filter papers were then transferred to a petri dish containing approximately $10^7$ cpm of $^{125}$I-labeled rabbit-IgG-antibodies (specific activity 7 mCi/mg) in PBS with an addition of 0.05% Tween 20 (PBST). After a 2-hour period of incubation at room temperature the filter papers were washed twice for 10 minutes in PBST and then dried. Autoradiographic analysis of the filter papers indicated the positive lambda clones which produced polypeptides binding the radioactive antibodies. These clones were selected on the original agar plate and analyzed again. Finally a clone called "lambda SPG1" was chosen for the subsequent procedures. A further possibility, in addition to using the above-enumerated systems, will of course be to propagate lambda SPGl in suitable strains of *E. coli* for producing the desired protein.

Example 2. DNA sequencing

The EMBL3a lambda vector has a structure such that DNA fragments ligated into BamlTI sites are flanked on both sides by SalI sites. Cleavage of lambda SPGL DNA with SAII gave two fragments of about 2.1 kilobase pairs (kb) and 12 kb respectively, deriving from the Streptococcal DNA fragment that had been inserted originally. These two fragments were ligated into SalI-cleaved pUC19 to thus produce the two recombinant plasmids pSPGI and pSPG8 containing 2.1 kb and 12 kb fragments respectively. Transformants of *E. coli* HB101 containing the said respective plasmids were cultured in Luria broth (Maniatis et al.) with addition of ampicillin to a final concentration of 50 micrograms/ml, whereupon the cell lysate (Lbfdahl et al., Proc. Natl. Acad. Sci. USA 80 (1983), p. 697–701) was tested for IgG-binding activity. This was done by means of the hemagglutination test (Guss et al., Eur. J. Biochem. 153 (1985) p. 579–585). An *E. coli* clone containing the plasmid pSPGI was positive in this test.

The plasmid pSPGl which contained an IgG binding portion of the protein G gene from Streptococcus G148 was digested with appropriate restriction enzymes; DNA fragments thus formed were cloned into the replicative form of the phage M13 and were then transformed into *E. coli* strain JM105. The nucleotide sequence of the inserted DNA fragments was analyzed by means of the so-called dideoxy method (Sanger F., Nicklen, S. and Coulson, AR. (1977), Proc. Natl. Acad. Sci. USA 74, 5463–5467).

Figure 1A:
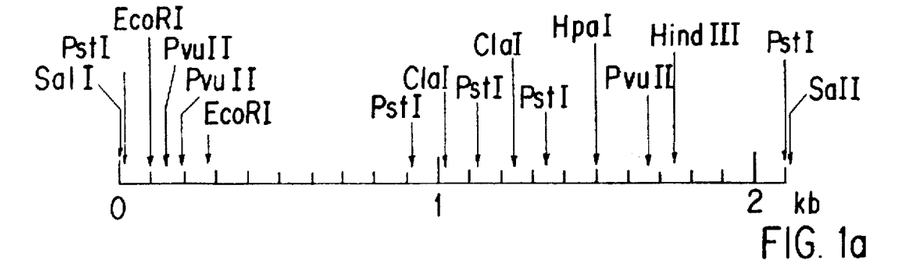
FIG. 1a shows the restriction map of pSPG1 containing an IgG binding portion of the protein G gene from Streptococcus G148.
Figure 1B:
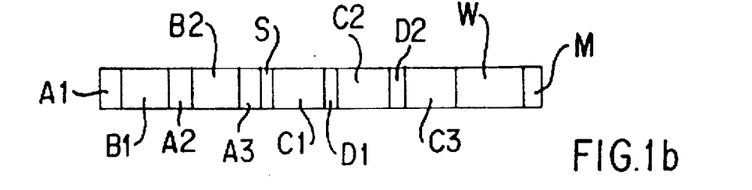
FIG. 1b shows repetitive structure of the DNA sequence.
Figure 2A:
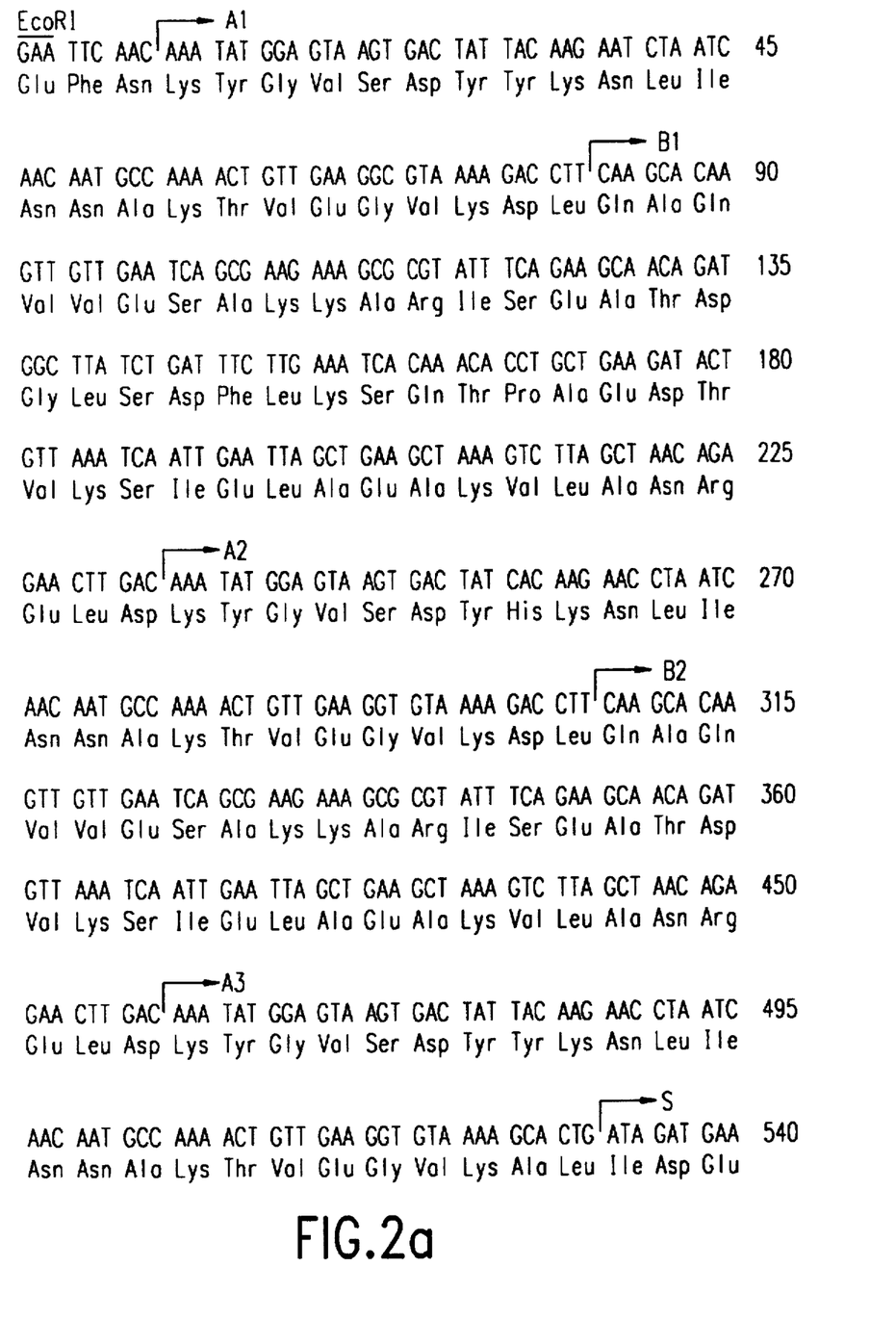
FIGS. 2a–2c shows the complete sequence of the EcoRI/HindIII fragment shown in FIG. 1(a).
Figure 2B:
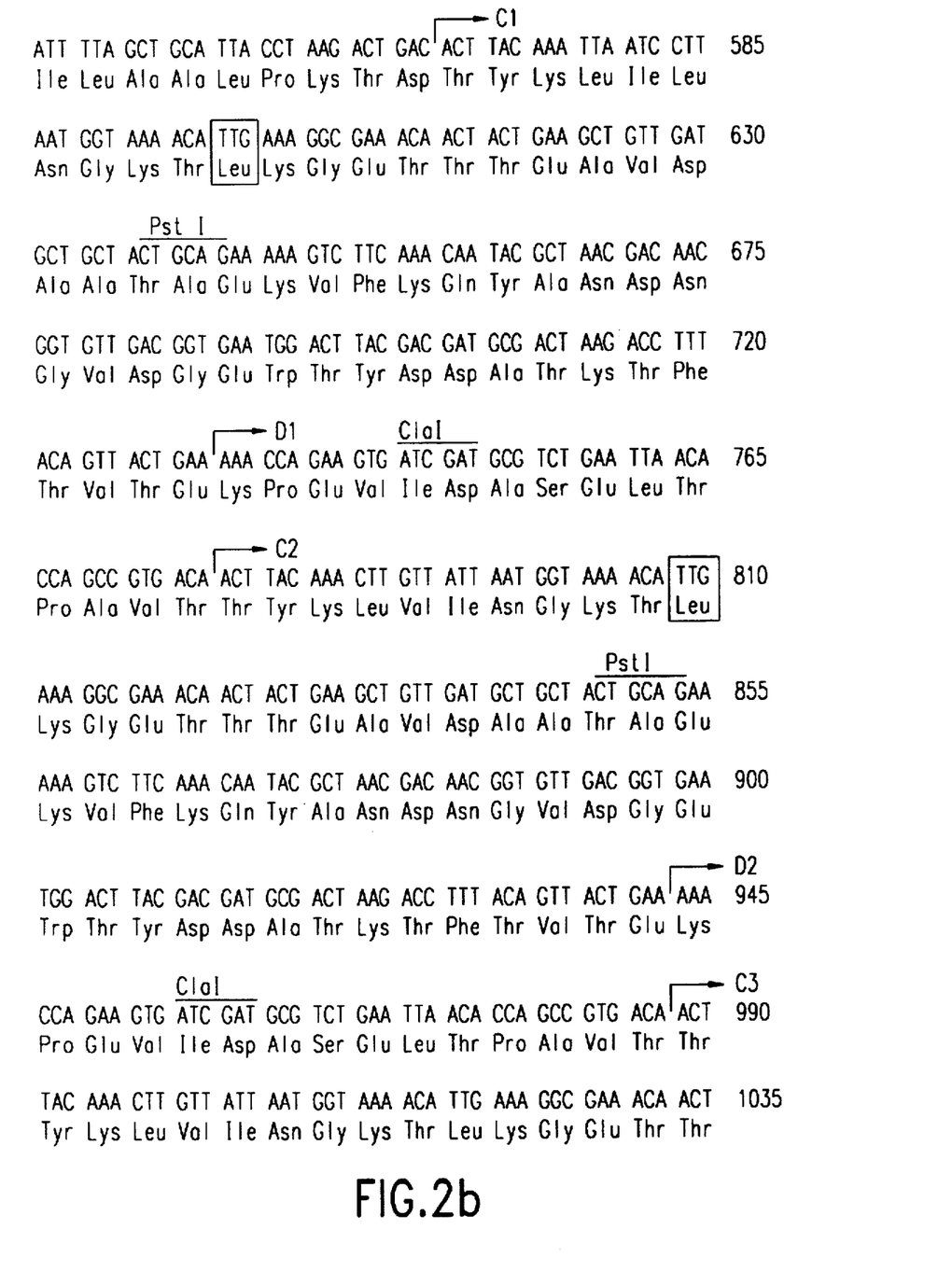
Figure 2C:
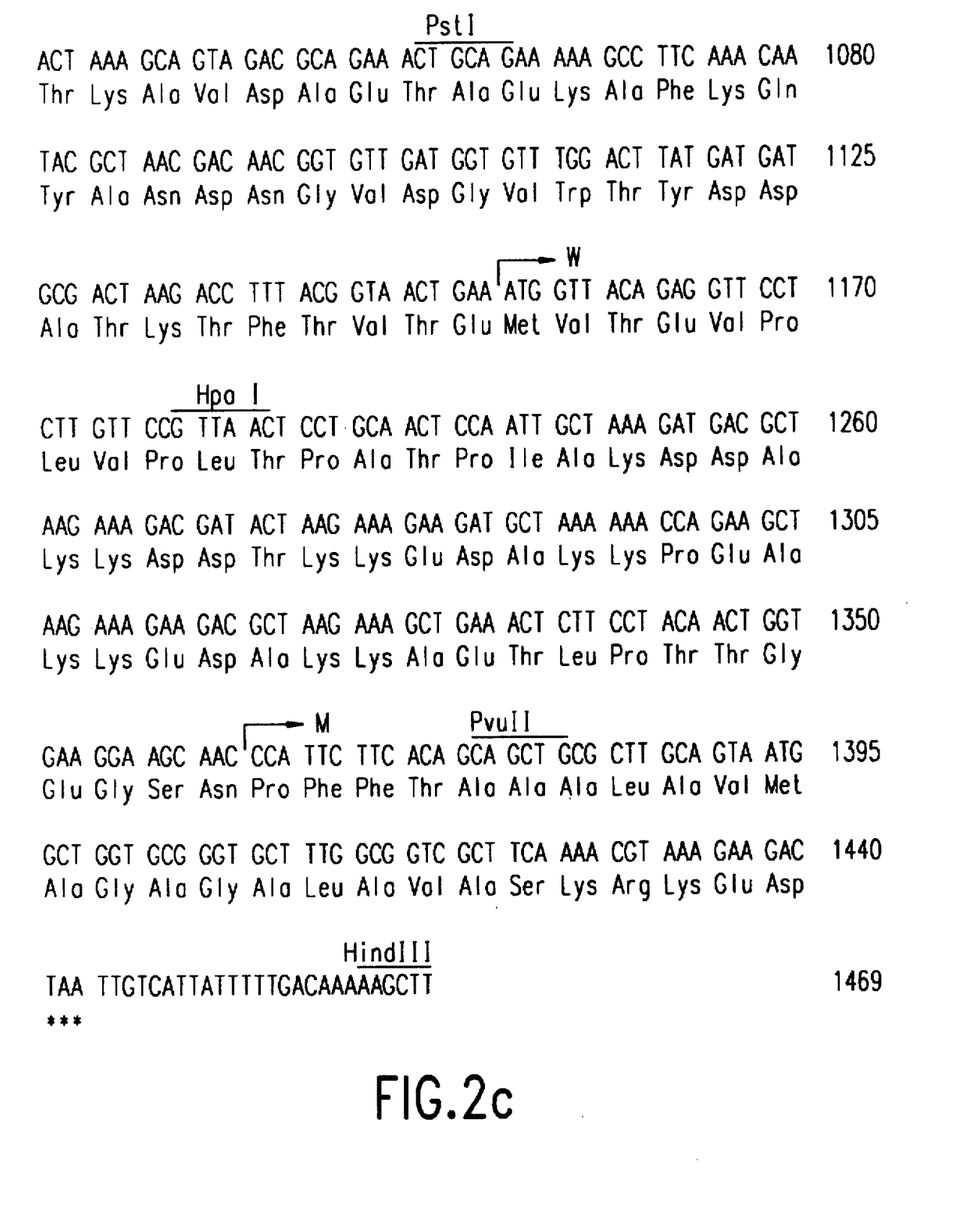

FIG. 1(a) shows the restriction map of PSPG1. A 1.5 kb EcoRI/HindIII fragment covering the range from 0.28 to 1.73 kb in FIG. 1(a) was cloned into pUC18 and pUC19 to thus give pSPG2 and pSPG3 respectively. The complete sequence of these is shown in FIG. 2. The regions that can be located in this sequence are set forth in FIG. 1(b) showing repetitive structures A1, A2 and A3 coding for 24 amino acids each and interrupted by sequences B1 and B2 (51 amino acids) which too are repetitive. A so-called spacer region S is followed by repetitive regions C1, C2 and C3 corresponding to 55 amino acids each and interrupted by regions D1 and D2 (15 amino acids). Next follows a hydrophilic portion, W, which has a structure similar to that of the so-called $X_r$ region of the protein A system (Guss et al. (1984) Eur. J. Biochem. 138, p. 413–420).

Figure 1C:
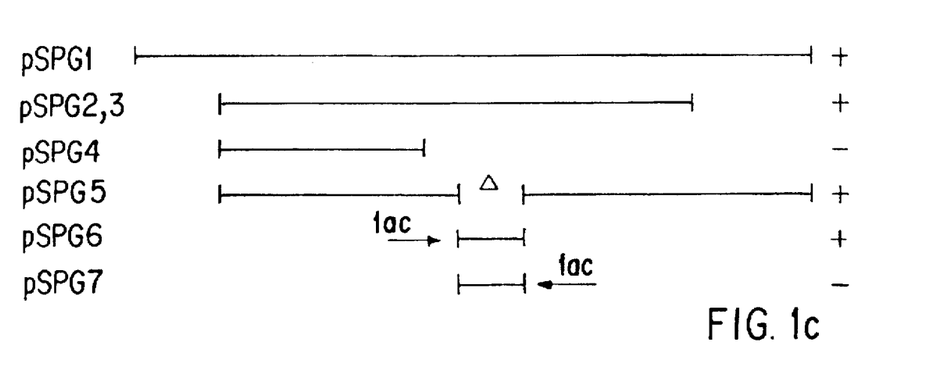
FIG. 1c shows subclones coding for an IgG binding product (+) or not coding for an IgG binding product (−).

Results obtained from amino acid analysis of the products from pSPG1, pSPG2 and pSPG3 (FIG. 1c) when compared with the protein A system indicated that both the W and the M regions are involved in cell wall—cell membrane interaction. The other regions could be subjected to a closer study with the aid of a number of subclones, pSPG4–pSPG7 (FIG. 1c). In that Figure, sequences coding for an IgG-binding product are indicated by means of a "+" sign, the rest being indicated by a "−" sign. It was found that pSPG4 and pSPG7 coded for non-binding products; so the part of the sequence expressing binding polypeptides is located in the C regions, that is, C1, C2 and C3.

Figure 3:
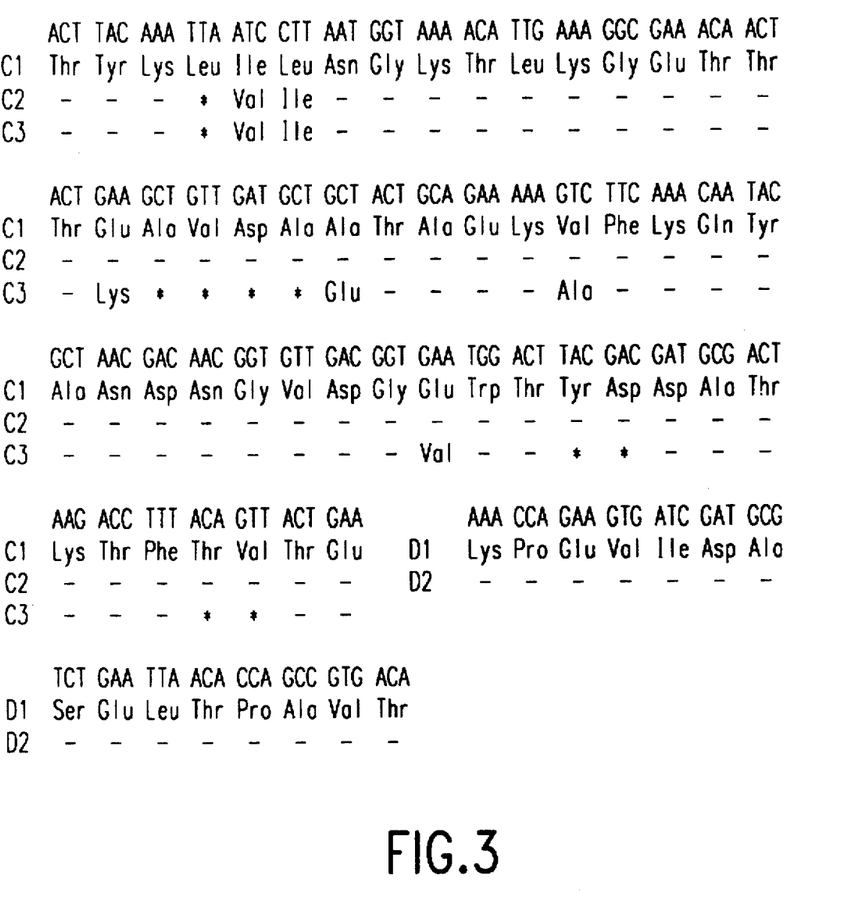
FIG. 3 compares the homologous regions C1, C2, and C3, and homologous regions D1 and D2.

FIG. 3 compares the homologous regions C1, C2, C3, as well as regions D1 and D2. The Figure shows the amino acid sequence of C1 and D1 and marks out the occurrences of deviations therefrom in C2 and C3, and D2 respectively. Cases where a different nucleotide sequence codes for the same amino acid are indicated by "*". As will be seen there are only a very few instances where deviations in nucleotide sequence have been such as to result in expression of a different amino acid.

Example 3

(a) Purification of protein G from Streptococcus G148

The bacterium was cultured in a tryptone medium (see above) in a 12-liter fermenter. At the end of the logarithmic phase the bacteria were harvested by centrifugation. The yield was about 100 g of bacteria (wet weight). Liberation of the cell wall protein (protein G) from the bacteria was carried out in the manner described by Björck and Kronvall (reference above). In short, this comprises suspending the bacteria (10% weight/volume) in 10 mM trishydroxyethyl aminomethane (Tris), pH 8.0. For digesting the bacteria we added per ml of bacteria suspension 100 microliters of 0.4M L-cycteine (Sigma) and 80 micrograms of papain (Sigma, p-3125) dissolved in the same buffer. The mixture was incubated for 1 hr at 37° C. on a shaking table. For stopping the reaction iodoacetamide (Sigma) was added to a final concentration of 6 m/M. The supernatant, about 1 liter, was removed from the mixture by centrifugation, whereupon protein G was isolated by means of chromatographic separation.

In a first step, the pH of the sample was adjusted to pH 8.0 with NaOH, and then 100 ml of DEAE Sephacel (Pharmacia AB) equilibrated in 10 mM Tris (HCl), pH 8.0, were added. The mixture was stirred for 2 hrs whereupon the gel after having been washed with the equilibrating buffer was packed onto a column (K26/40, Pharmacia AB) which was eluted with a linear gradient, 500 ml, from 0 to 0.5M NaCl. The fractions containing protein G were detected by immunodiffusion against polyclonal IgG and were then pooled to form one sample.

In a second step, the said sample (about 220 ml) was diluted with an equal volume of PBST (30 mM Na-PO$_4$, 0.12M NaCl, pH 7.2, and containing 0.05% of Tween 20) and was mixed with 15 ml of IgG-Sepharose® 4B (Pharmacia AB). After 2.5 hrs of stirring the gel was washed on a glass filter and packed into a K16/20 column (Pharmacia AB). The protein was then liberated from the gel bed by isocratic elution with 0.1M glycine (HCl), pH 2.5 (flow rate 10 ml/hr). Desalting was effected with the aid of a PD-10 column (Pharmacia AB) down to 30 mM Na-PO$_4$, pH 7.2.

The protein was then characterized by analytical chromatography on a Mono Q HR 5/5 column (Pharmacia AB). The chromatograms indicated that the results were very much dependent on the manner in which the papain extraction had been carried out. Two prominent peaks plus some lesser peaks of protein G activity were noted. SDS electrophoresis revealed two protein bands corresponding to MW 10,000 and MW 15,000. Table 1 sets forth the reactivity of protein G from enzyme-digested Streptococcus G148 together with the corresponding values obtained with the procedure according to Example 3(b) below.

(b) Purification and characterization of protein G produced by an *E coli* strain An *E. coli* strain containing the plasmid pSPG1 (see above) was employed for the production of protein G.

The bacterium was cultured in a 12-liter fermenter in a standard *E. coli* medium (see above). At the end of the logarithmic phase the cells were separated by centrifugation. About 560 g of bacteria (wet weight) were obtained. These were resuspended in 560 ml PBS and shredded in a mill (Dyno-Mill Type KDL, Willy A. Bachofen AG, Maschinenfabrik, Switzerland). Milling was performed with 0.1–0.2 mm glass beads with stirring at a rate of 3,000 rev./min. and a flow rate of 5.7 lit./hr. The supernatant, about 1,480 ml, was separated by centrifugation.

Chromatographic purification was carried out in a manner analogous to that described in Example 3(a), the principal difference being that the affinity chromatographic step was performed prior to the ion exchange step.

When the purified protein was analyzed it was found that there were two main fractions of molecular weight 30,000 and 40,000 respectively. This should be compared to the values 10,000 and 15,000 respectively obtained in the case of the papain-digested Streptococcus. However, the IgG reactivity was the same; see Table 1.

Table 2 gives a comparison of the amino acid compositions of (i) protein G from papain-extracted Streptococcus G148 (Example 3a) and (ii) protein produced by *E. coli* (Example 3b).

Table 3 compares protein A and protein G in respect of their affinity for various immunoglobulins. The Table sets forth the amount of each immunoglobulin required for 50% inhibition of binding between enzyme-conjugated polyclonal rabbitIgG and immobilized protein A or protein G respectively. In view of the differences in affinity as evidenced by the results, the aforesaid protein A–protein G fusion protein is an interesting application of the present invention as shown in Example 4 (below). Correspondingly also fusion proteins are contemplated which contain active fragments of protein A and protein G—"active" in respect of immunoglobulin-binding capacity.

Example 4.

Constructions of plasmid vectors encoding immunoglobulin binding activities of protein G or a fusion protein composed of protein A and protein G In the construction work described in this Example additional manufacturers (Pharmacia AB, Sweden, and IBI (International Biotechnologies Inc., New Haven)) other than those mentioned above were used to supply for the different restriction endonucleases and the T4 DNA polymerase. The enzymes were used according to the suppliers recommendations. Between each step in the construction procedure inactivation and removal of the used enzyme (using phenol/ chloroform extraction) was performed, followed by ethanol precipitation of the DNA. Finally, the DNA sample was resuspended in suitable buffer.

The *E. coli* strain TGI (Carter et al (1985) Nucleic Acids Res. 12: 4431-4443) was used. After transformation of the ligated samples into *E. coli* cells the recombinant clones were selected for ampicillin resistance.

Figure 4:
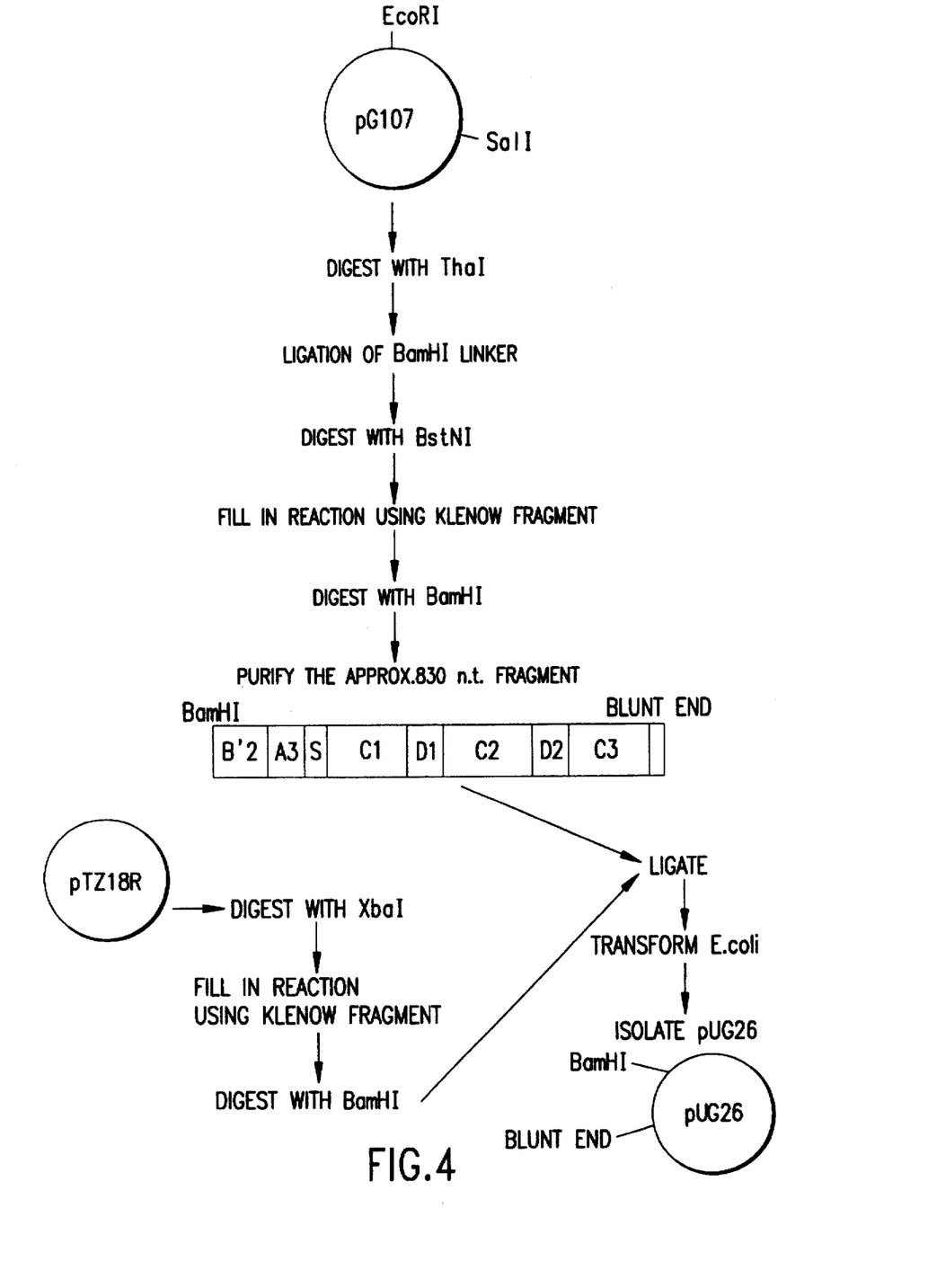
FIG. 4 is a schematic drawing showing the different steps to construct pUG26.

Construction of pUG26. A subclone called pG107 containing the approx. 1.8 kb EcoRI/SalI fragment (position 0.3 to 2.1 in FIG. 1 C) from pSPG1 (Example 2) inserted between the EcoRI/SalI sites in pBR322, was used to isolate a DNA fragment coding for the immunoglobulin binding regions of protein G. As shown schematically in FIG. 4 the pG107 was digested with ThaI followed by ligation of a 8-mer oligonucleotid adapter (Pharmacia AB, Sweden, cat.no. 27-7730-01) with the recognition site for BamHI. The ligated sample was cleaved with BstNI followed by incubation with Klenow fragments and the four deoxynucleotides to fill in the BstNI restriction site thereby generating blunt ends. The latter procedure was followed by BamHI treatment and the sample was subjected to electrophoresis in an agarose gel. A DNA fragment of approx. 830 n.t. was cut out, eluted and purified. A schematic drawing of this fragment is shown in FIG. 4. This fragment was ligated into pTZ18R (Pharmacia AB, Sweden, cat.no. 27-4984-01) earlier digested with XbaI followed by incubation with Klenow fragment and the four deoxynucleotides to fill in the XbaI restriction site generating a blunt end and finally digestion with BamHI. Thus, the purified BamHI/blunt end fragment, containing the immunoglobulin binding regions of protein G was ligated into pTZ18R with generated BamHI/blunt ends. After ligation the sample was transformed into freeze competent *E. coli* cells and a clone positive in production of protein G, called pUG26, harbouring the protein G fragment was isolated. A schematic drawing of pUG26 is shown in FIG. 4.

Construction of pUG27. A derivate of pTZ18R was constructed, containing an oligonucleotide called Universal Translation Terminator (Pharmacia AB, Sweden, cat.no 27-4890-01) here abbreviated as UTL. The construction of the pTZ18RUTL vector is also schematically shown in FIG. 5. The pTZ18R was digested with PstI followed by incubation with T4 DNA polymerase to digest the sticky ends generating blunt ends to which UTL adapters were ligated. After ligation the sample was transformed into freeze competent *E. coli* cells and a clone harbouring one UTL-adapter inserted into the modified PstI site was isolated and called pTZ18RUTL.

Figure 5:
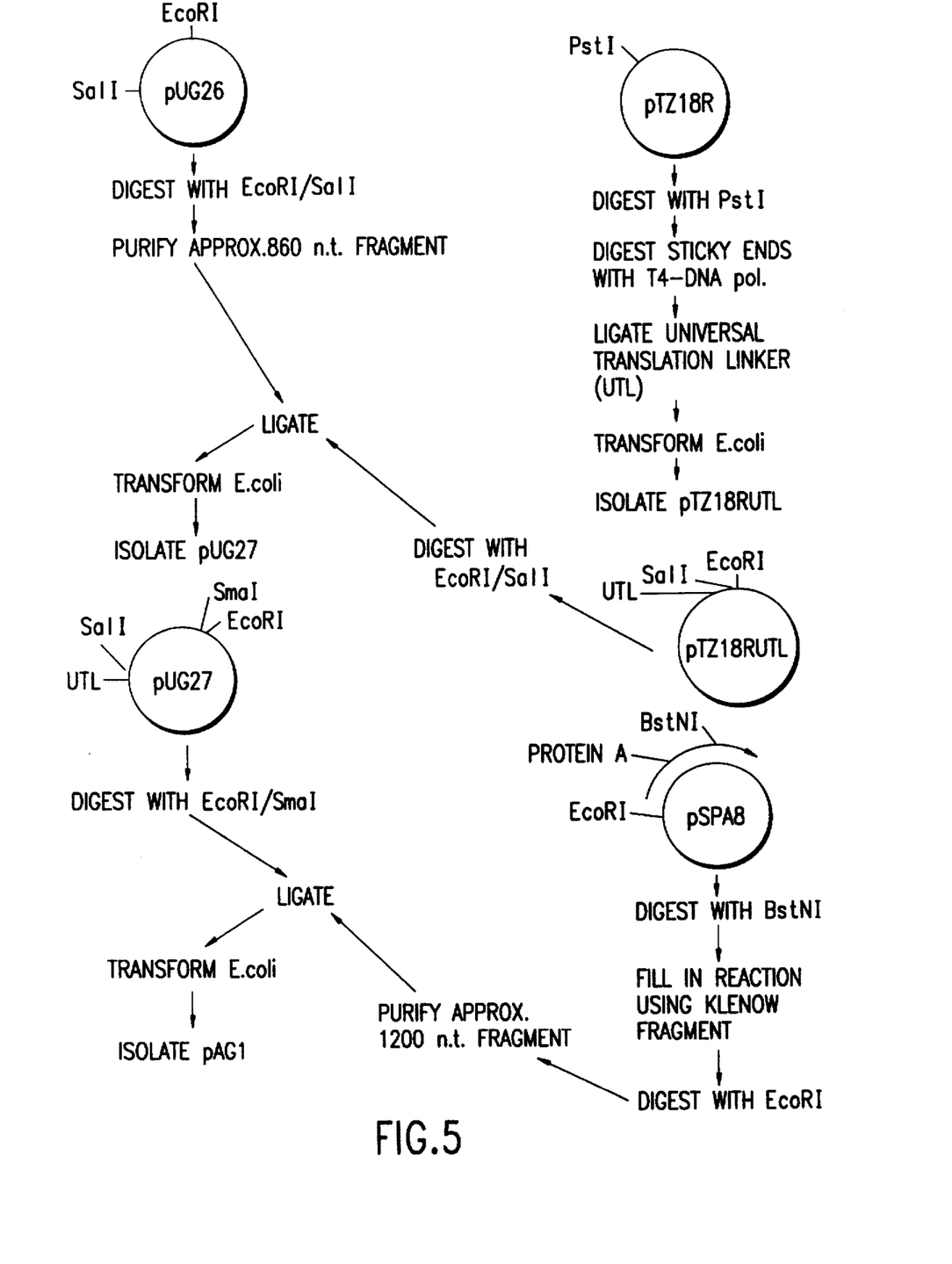
FIG. 5 is a schematic drawing showing the different steps to construct pUG27, pTZ18UTL, and pAG1.

Plasmid pUG26 was digested with EcoRI/SalI and the digested sample was subjected to electrophoresis in an agarose gel and a DNA fragment of approx. 860 n.t. encoding the immunoglobulin binding regions of protein G was cut out, eluted and purified. This fragment was ligated into a EcoRI/SalI digested pTZ18RUTL vector (FIG. 5).

After ligation the sample was transformed into freeze competent *E. coli* cells and a clone positive in production of protein G, called pUG27 was isolated. A schematic drawing of pUG27 is shown in FIG. 5.

Figure 6:
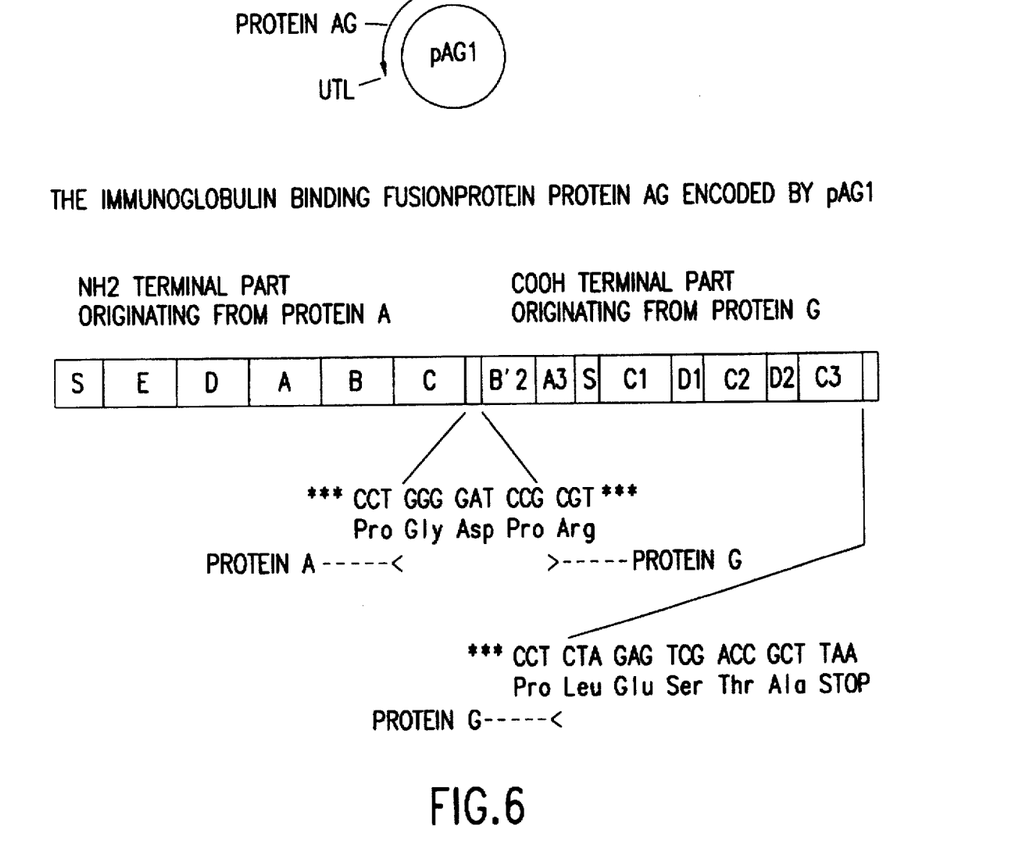
FIG. 6 is a schematic drawing showing the pAG1 construct and a more detailed drawing of the encoded fusion molecule, protein AG, with the different regions. The different junctions are shown in detail.

Final construction of the pAG1. To isolate a DNA fragment containing the protein A promoter and ribosomal binding sequences together with the part that encodes the signal sequence and the immunoglobulin binding regions E, D, A, B and C, a plasmid called pSPA8 (Uhlen et al 1983. Gene, 23, 369-378) was used. This plasmid was digested with BstNI followed by incubation with Klenow fragment and the four deoxynucleotides to fill in the BstNI site thereby generating blunt ends. This was followed by digestion with EcoRI. After digestion the sample was subjected to electrophoresis in an agarose gel. A DNA fragment of approx. 1200 n.t. containing the above described regions of protein A was cut out, eluted and purified. This fragment was ligated into EcoRI/SmaI digested pUG27 (FIG. 5). After ligation the sample was transformed into freeze competent *E. coli* cells and a clone with the plasmid pAG1 was isolated harbouring the protein A fragment (FIG. 5). The pAG1 plasmid encodes a fusion molecule which is schematically drawn in FIG. 6 where a more detailed description of the different junctions is included.

Construction of a plasmid vector designated to express extracellular protein G

Figure 7:
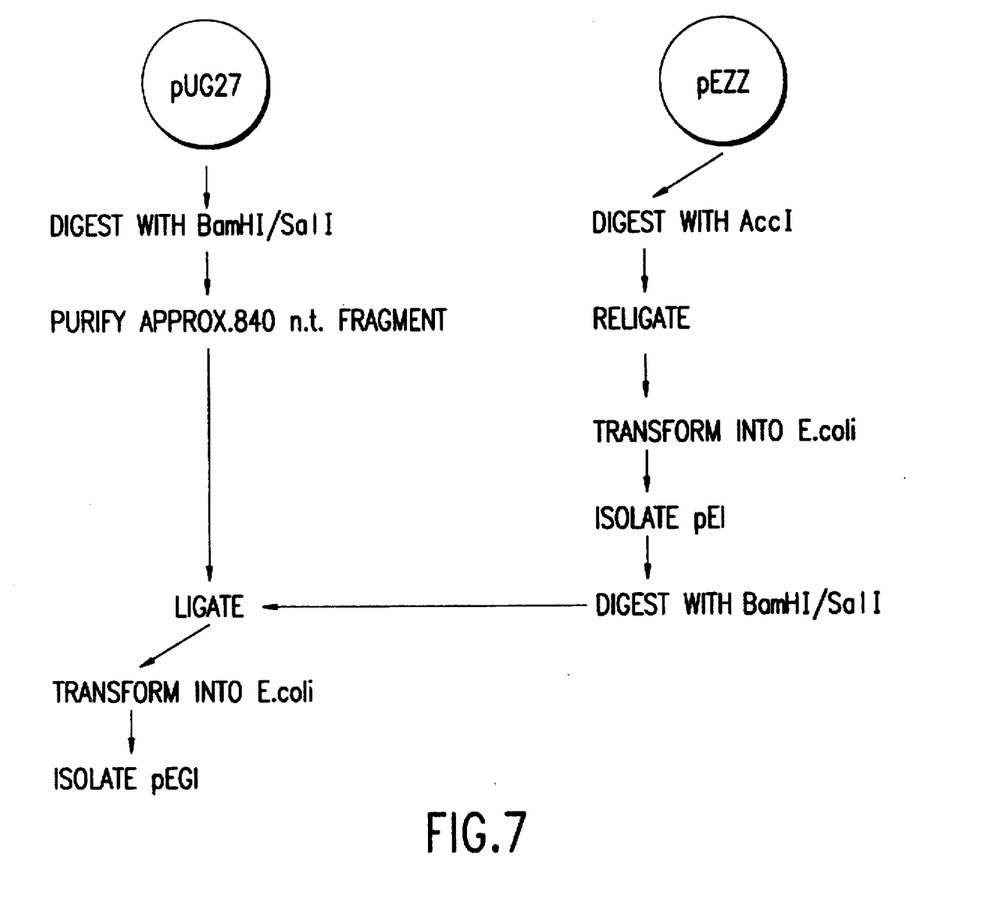
FIG. 7 is a schematic drawing showing the different steps to construct pEG1.

The construction of the pE1 plasmid is schematically shown in FIG. 7. The pEZZ plasmid (Nilsson et al (1986) Protein Engineering, in press) was used. The pEZZ plasmid was digested with AccI followed by religation at low concentration (1 mg/l) to delete the region between the AccI sites. The ligated sample was transformed into freeze competent *E. coli* cells and a clone, called pE1, was isolated, lacking the two ZZ regions.

Plasmid pUG27 was digested with BamHI/HindIII and the digested sample was subjected to electrophoresis in an agarose gel and a DNA fragment of approx. 840 n.t. containing the immunoglobulin binding regions of protein G was cut out, eluted and purified. This fragment was ligated into BamHI/HindIII digested pE1 plasmid.

Thus, after the ligation of the BamHI/HindIII fragment of pUG27 into BamHI/HindIII digested pE1, the sample was transformed into freeze competent *E. coli* cells and a clone positive in production of protein G, called pEG1, harbouring the protein G fragment was isolated.

Expression and purification of the pAG1 and pEG1 derived proteins

*E. coli* cells harbouring the pAG1 and pEG1 plasmid respectively were grown in 1 liter of *E. coli* liquid culture medium (see above) supplemented with ampicillin (final concentration 100 microgram/mil) over night at 37° C. The growth medium from the over night cultures was recovered by centrifugation and subsequently subjected to IgG affinity chromatography according to Nilsson et al 1986 (Protein Engineering, in press).

The purified proteins obtained were analysed using SDS-PAGE and the molecular weights agreed with those calculated from the deduced nucleotide sequence (approx. 31000 for the pEG1 gene product and approx. 66000 for the pAG1 gene product).

Comparative immunoglobulin binding studies

The immunoglobulin binding affinities of the pAG1 and pEG1 encoded proteins, here called protein AG and protein G respectively, were compared to commercial protein A obtained from Pharmacia AB, Sweden. The immunoglobulin binding activity of the different proteins were analyzed using a competitive ELISA technique according to Guss et al (EMBO J. 5, 1567-1575 (1986)). The different immunoglobulins were tested for their ability to inhibit the binding between alkaline phosphatase-conjugated polyclonal rabbit IgG antibodies and immobilized commercial protein A and the proteins AG and G. The results of these studies are presented in Tables 4 and 5. Note that the figures in these tables have been standardized against the binding activity to polyclonal rabbit IgG.

The figures in Table 4 show that protein A has a higher affinity than protein G derived from pEG1 to polyclonal IgG from human, guinea-pig, dog, pig and mouse. In contrast protein G derived from pEG1 shows stronger interaction with polyclonal IgG from cow, horse, goat and sheep. All three proteins interact with the same relative strength to polyclonal rat IgG and do not bind to polyclonal chicken IgG. Table 4 also presents the binding activity of the fusion protein AG expressed from pAG1. Protein AG has affinity to all species of polyclonal IgG which bind protein A and/or protein G. Thus, as shown in Table 4 protein AG combines both protein A and G binding activity.

The affinities of proteins A, G and AG to different human myeloma immunoglobulins are presented in Table 5. Protein A shows high affinity to IgG1, IgG2 and IgG4 but not to IgG3, in contrast to protein G which shows high affinity to all IgG subclasses. Protein AG shows a high affinity to all IgG subclasses except for IgG3 to which it binds with less affinity than protein G but higher than protein A. None of the proteins A, G or AG shows any affinity to the myeloma of the IgM and IgD classes.

Conclusions

The results presented in this example show that plasmid pEG1 encodes a protein with the corresponding IgG-binding specificity as protein G encoded by pSPG1.

Furthermore, the fusion protein AG, encoded by pAG1 has in one molecule the combined IgG-binding specificity of the two separate proteins A and G.

TABLE 1

Immunoglobulin affinity of protein G from papain-extracted Streptococcus G148 and from E. coli containing a plasmid coding for protein G according to Examples. Assays have been carried out by way of immunodiffusion and their results are set forth as: direct precipitation, (2); ability to inhibit precipitation reaction between polyclonal bovine IgG and protein G (1); neither inhibition nor precipitation (0).

| Ig class | Streptococci | E. coli |
|---|---|---|
| Polyclonal IgG | | |
| human | 2 | 2 |
| rabbit | 1 | 1 |
| cow | 2 | 2 |
| horse | 2 | 2 |
| goat | 2 | 2 |
| guinea pig | 2 | 2 |
| sheep | 2 | 2 |
| dog | 0 | 0 |
| pig | 2 | 2 |
| rat | 0 | 0 |
| mouse | 2 | 2 |
| chicken | 0 | 0 |
| Monoclonal murine Ig[1] | | |
| 1 (human IgE) | 1 | 1 |
| 1 (tpa) | 2 | 2 |
| 2a (Chl, C.C17) | 1 | 1 |
| 2a (Gc, 5293.A57) | 2 | 2 |
| 2a (Gc, R11.B6) | 2 | 2 |
| 2a (Gc, W16.A30) | 2 | 2 |
| 2b (Gc, C3.D1) | 2 | 2 |
| 2b (Gc, F6.C6) | 2 | 2 |
| 3 (Gc, C3.D14) | 2 | 2 |
| 3 (Gc, V15.A13) | 2 | 2 |
| Human myeloma proteins | | |
| IgG 1 lambda | 2 | 2 |
| 1 kappa | 2 | 2 |
| 2 lambda | 2 | 2 |
| 2 kappa | 2 | 2 |
| 3 lambda | *) | *) |
| 3 kappa | 2 | 2 |

TABLE 1-continued

Immunoglobulin affinity of protein G from papain-extracted Streptococcus G148 and from E. coli containing a plasmid coding for protein G according to Examples. Assays have been carried out by way of immunodiffusion and their results are set forth as: direct precipitation, (2); ability to inhibit precipitation reaction between polyclonal bovine IgG and protein G (1); neither inhibition nor precipitation (0).

| Ig class | Streptococci | E. coli |
|---|---|---|
| 4 lambda | 2 | 2 |
| 4 kappa | 2 | 2 |
| IgM | 0 | 0 |
| IgA | 0 | *) |
| IgD | 0 | 0 |

*)Not determined
[1]As identified by names of individual monoclonals

TABLE 2

Comparison of amino acid contents of purified protein G (as determined in the two principal protein fractions) when derived from (i) papainextracted Streptococcus G148 and (ii) E. coli carrying a plasmid coding for protein G according to Example 3(b). Results are set forth in mole percent.

| | Streptococci G148 | | E. coli | |
|---|---|---|---|---|
| Amino acid | Fract I | Fract II | Fract I | Fract II |
| asparagine + aspartic acid | 13.8 | 12.7 | 7.6 | 8.4 |
| threonine | 18.2 | 21.5 | 15.8 | 18.3 |
| serine | 2.0 | — | 2.5 | 2.4 |
| glutamine + glutamic acid | 12.0 | 9.4 | 10.7 | 10.9 |
| proline | 3.2 | 2.1 | 6.5 | 4.8 |
| glycine | 5.9 | 6.6 | 6.0 | 6.1 |
| alanine | 11.3 | 10.7 | 15.9 | 15.5 |
| valine | 8.6 | 10.4 | 8.2 | 8.6 |
| methionine | — | 1.7 | 1.1 | 0.5 |
| isoleucine | 2.3 | 1.7 | 1.9 | 1.7 |
| leucine | 4.8 | 4.7 | 4.4 | 4.1 |
| tyrosine | 4.4 | 4.7 | 2.7 | 3.0 |
| phenylalanine | 2.9 | 3.0 | 3.0 | 3.0 |
| lysine | 10.6 | 10.7 | 12.7 | 12.1 |
| histidine | — | — | 0.4 | 0.2 |
| arginine | — | — | 0.6 | 0.4 |
| cysteine | 1) | 1) | 1) | 1) |
| tryptophan | 1) | 1) | 1) | 1) |

[1]Not determined

TABLE 3

Comparison of protein A and protein G in respect of their affinity for various immunoglobulins. The Table sets forth the amount of each immunoglobulin required for 50% inhibition of binding between enzyme-conjugated polyclonal IgG and immobilized protein A or protein G respectively. Non-reactivity is designated by "—".

| | Amount (ng) required for 50% inhibition | |
|---|---|---|
| Immunoglobulin | Protein G | Protein A |
| Polyclonal IgG | | |
| human | 556 | 263 |
| rabbit | 151 | 154 |
| cow | 294 | 3125 |
| horse | 227 | >10000 |
| goat | 217 | 1333 |
| guinea pig | 2500 | 454 |
| sheep | 357 | >10000 |
| dog | 5556 | 400 |

TABLE 3-continued

Comparison of protein A and protein G in respect of their affinity for various immunoglobulins. The Table sets forth the amount of each immunoglobulin required for 50% inhibition of binding between enzyme-conjugated polyclonal IgG and immobilized protein A or protein G respectively. Non-reactivity is designated by "—".

| Immunoglobulin | Amount (ng) required for 50% inhibition | |
|---|---|---|
|  | Protein G | Protein A |
| pig | 456 | 179 |
| rat | >10000 | — |
| mouse | 1020 | 333 |
| chicken | — | — |
| Human myeloma proteins | | |
| IgG  1 lambda | 250 | 174 |
|       1 kappa | 185 | 111 |
|       2 lambda | 208 | 256 |
|       2 kappa | 227 | 256 |
|       3 kappa | 345 | 7404 |
|       4 lambda | 210 | 635 |
|       4 kappa | 256 | 250 |
| IgM | — | — |

TABLE 4

Relative amounts of polyclonal IgG from different species required to give a 50% inhibition of the binding between enzyme labeled rabbit polyclonal IgG and immobilized proteins A, G or AG[*].

| Species | A | G | AG |
|---|---|---|---|
| Rabbit | 1.0 | 1.0 | 1.0 |
| Human | 0.7 | 1.0 | 1.4 |
| Cow | 5.0 | 1.5 | 1.9 |
| Horse | >30 | 0.5 | 7.1 |
| Goat | 3.3 | 3.0 | 2.9 |
| Guinea-pig | 0.7 | 13.0 | 1.7 |
| Sheep | >30 | 1.5 | 11.3 |
| Dog | 0.3 | 6.0 | 0.9 |
| Pig | 0.3 | 3.6 | 1.0 |
| Rat | >30 | >30 | >30 |
| Mouse | 12.0 | >30 | 12.0 |
| Chicken | — | — | — |

[*]Key to the table: The figures have been standardized to polyclonal rabbit IgG.

TABLE 5

Relative amounts of different human myeloma immunoglobulins required to give a 50% inhibition of the binding between enzyme labeled rabbit polyclonal IgG and immobilized proteins A, G or AG[*].

|  | A | G | AG |
|---|---|---|---|
| IgG1 lambda | 0.2 | 0.5 | 0.4 |
| IgG1 kappa | 0.2 | 0.5 | 0.4 |
| IgG2 lambda | 1.3 | 2.0 | 1.0 |
| IgG2 kappa | 1.7 | 2.0 | 1.6 |
| IgG3 kappa | 22.0 | 1.0 | 8.0 |
| IgG4 lambda | 3.8 | 1.5 | 0.7 |
| IgG4 kappa | 0.3 | 1.5 | 0.7 |
| IgM | — | — | — |
| IgD | — | — | — |

[*]Key to the table: The figures have been standardized to polyclonal rabbit IgG.

We claim:

1. A fusion protein or polypeptide having the IgG binding specificities of protein A and protein G, comprising a sequence having the IgG binding specificity of protein G fused to a sequence having the IgG binding specificity of protein A.

2. A fusion protein as in claim 1, produced by expression of a recombinant DNA molecule which comprises a nucleotide sequence encoding a protein or polypeptide having the IgG binding specificity of protein G, and a further nucleotide sequence operably linked thereto, said further nucleotide sequence encoding a protein or polypeptide having the the IgG binding specificity of protein A.

* * * * *